United States Patent [19]

Thornton

[11] Patent Number: 5,891,090
[45] Date of Patent: *Apr. 6, 1999

[54] PERFUSION DILATATION CATHETER WITH EXPANDED SUPPORT COIL

[75] Inventor: Troy L. Thornton, San Francisco, Calif.

[73] Assignee: Advanced Cardiovascular Systems, Inc., Santa Clara, Calif.

[*] Notice: The term of this patent shall not extend beyond the expiration date of Pat. No. 5,573,509.

[21] Appl. No.: 796,881

[22] Filed: Feb. 7, 1997

Related U.S. Application Data

[63] Continuation-in-part of Ser. No. 589,910, Jan. 23, 1996, abandoned, which is a continuation of Ser. No. 212,225, Mar. 14, 1994, abandoned.

[51] Int. Cl.[6] .................................................. A61M 29/00
[52] U.S. Cl. .............................................................. 604/102
[58] Field of Search ............................ 604/96, 102, 264, 604/280, 282; 606/192, 194

[56] References Cited

U.S. PATENT DOCUMENTS

| 3,938,529 | 2/1976 | Gibbons | 604/282 X |
|---|---|---|---|
| 5,195,971 | 3/1993 | Sirhan | 604/96 |
| 5,201,723 | 4/1993 | Quinn | 604/264 |
| 5,279,562 | 1/1994 | Sirhan et al. | 604/96 |
| 5,328,472 | 7/1994 | Steinke et al. | 604/102 |
| 5,344,402 | 9/1994 | Crocker | 604/96 |
| 5,383,890 | 1/1995 | Miraki et al. | 606/194 |
| 5,542,925 | 8/1996 | Orth | 604/102 |
| 5,554,114 | 9/1996 | Wallace et al. | 604/53 |
| 5,573,509 | 11/1996 | Thornton | 604/102 |
| 5,591,129 | 1/1997 | Shoup et al. | 604/96 |

FOREIGN PATENT DOCUMENTS

| WO 93/01856 | 2/1993 | WIPO . |
| WO 93/13826 | 7/1993 | WIPO . |
| WO 93/21985 | 11/1993 | WIPO . |

Primary Examiner—Wynn Wood Coggins
Assistant Examiner—Sharon Finkel
Attorney, Agent, or Firm—Heller, Ehrman, White & McAuliffe

[57] ABSTRACT

A balloon dilatation catheter having perfusion capabilities with an expanded helical support coil within the perfusion portion of the catheter shaft proximal to the balloon with the perfusion ports being defined by passageways through adjacent turns of the support coil. Elongated portions of an outer polymer jacket are removed, preferably by laser, to expose a plurality of turns of the support coil and define a number of perfusion ports between adjacent turns.

6 Claims, 4 Drawing Sheets

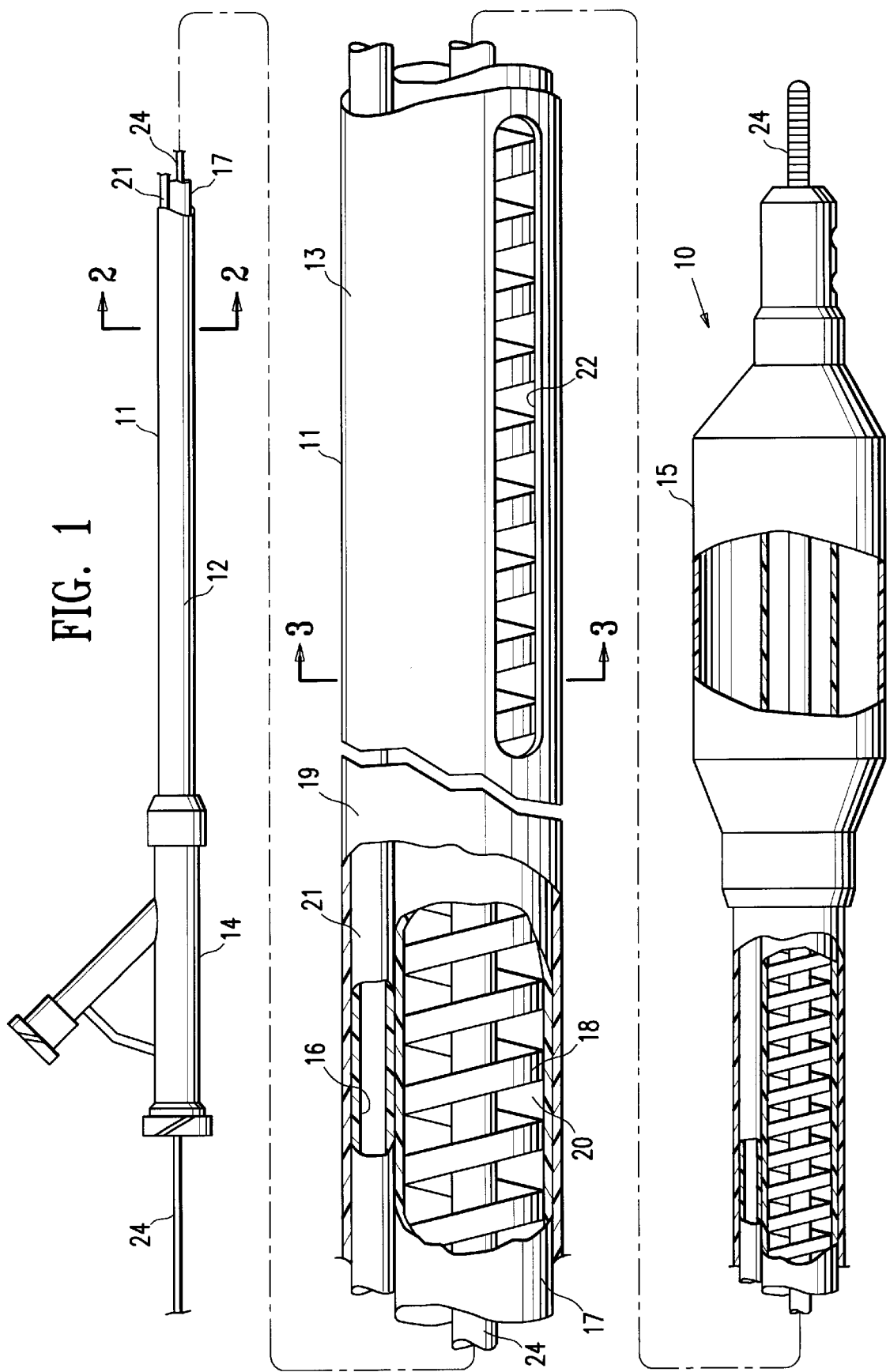

5,891,090

PERFUSION DILATATION CATHETER WITH EXPANDED SUPPORT COIL

RELATED APPLICATIONS

This application is a continuation-in-part application to application Ser. No. 08/589,910, filed on Jan. 23, 1996, entitled CATHETER PROVIDING INTRALUMINAL ACCESS, now abandoned, which is a continuation of application Ser. No. 08/212,225, filed Mar. 14, 1994, now abandoned, which are incorporated herein by reference.

BACKGROUND OF THE INVENTION

This invention generally relates to perfusion type dilatation catheters for use in percutaneous transluminal coronary angioplasty (PTCA).

In typical PTCA procedures a balloon dilatation catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures (e.g. generally 4–12 atmospheres) to dilate the stenosed region of the diseased artery. One or more inflations may be needed to effectively dilate the stenosis. After the dilatation of the first stenosis the catheter may be advanced further into the patient's coronary anatomy to dilate additional stenoses.

A high number of angioplasty procedures result in a dissected arterial lining which can cause an acute closure of the arterial passageway. In the latter instances a perfusion device must be advanced over the in-place guidewire to ensure adequate blood blow distal to the dissected lining until the lining can be resecured to the artery wall, coronary or a by-pass procedure commenced. Preferably, a dilatation balloon catheter with perfusion capabilities is advanced over the in-place guidewire until the balloon crosses the dissection and the balloon is inflated to press the dissected lining back into place against the arterial wall. With the balloon inflated, blood is caused to pass through a perfusion passageway through the balloon to discharge the blood distal to the catheter. The balloon is maintained in an inflated condition for sufficiently long periods of time, e.g. from about 0.5 to about 6 hours, for the natural healing process to resecure the dissected lining to the arterial wall.

Balloon catheters with perfusion capabilities have been available from Advanced Cardiovascular Systems, Inc. for a number of years, including the RX Perfusion Coronary Dilatation Catheter and the Lifestream Dilation Catheter which has met with much commercial success. Such catheters are described in U.S. Pat. No. 5,496,275 (Sirhan et al) and U.S. application Ser. No. 08/183,574, filed on Jan. 18, 1994 which are incorporated herein in their entirety. The perfusion catheters presently on the market are predominantly rapid exchange type dilatation catheters due to the frequent need to advance a perfusion catheter over an in-place guidewire when an acute occlusion occurs after the original dilatation catheter has been deflated and withdrawn from the stenotic region.

SUMMARY OF THE INVENTION

This invention is directed to a perfusion type dilatation catheter which has a flexible non-kinkable perfusion portion which does not require complicated manufacturing procedures characteristic of prior perfusion dilatation catheters.

The perfusion type dilatation catheter of the invention generally includes an elongated catheter shaft with proximal and distal shaft sections, a distal end, a distal guidewire port in the distal end, a proximal guidewire port spaced proximal to the distal end and an inflatable balloon on the distal shaft section. The catheter shaft has an inflation lumen extending from its proximal end to a location spaced proximal from the distal end of the catheter shaft and in fluid communication with the interior of the balloon. A guidewire receiving inner lumen is provided within the distal section extending between the proximal and distal guidewire ports.

In the distal shaft section, the perfusion portion proximal to the balloon is provided with an outer polymer jacket, an inner expanded helical support coil and a plurality of perfusion ports through the polymer jacket and disposed between adjacent turns of the helical support coil. In one presently preferred embodiment, an elongated portion of the outer jacket is removed along with any material between adjacent turns of the coil to define the perfusion ports between adjacent turns of the coil in the distal shaft section. A pair of elongated portions of the outer jacket can be removed about the same axial location without fear of the shaft collapsing, i.e. kinking, at the location because the helical coil supports the catheter shaft at this location. Thus, effective perfusion of oxygenated blood through the guidewire receiving lumen of the dilatation catheter can be maximized with no significant loss of mechanical properties of the catheter shaft while maintaining good flexibility in the distal shaft section. The expansion of the helical support coil is preferably controlled so that the spacing between adjacent turns of the coil is insufficient to allow the passage of a guidewire therethrough.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a balloon dilatation embodying features of the invention.

DETAILED DESCRIPTION OF THE INVENTION

Figure 3:
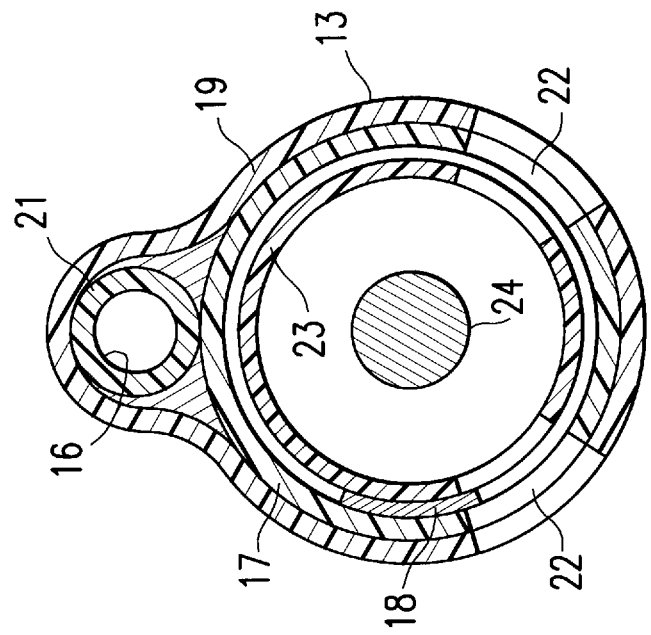
FIG. 3 is a transverse cross-sectional view of the catheter shown in FIG. 1 taken along the lines 3—3.
Figure 2:
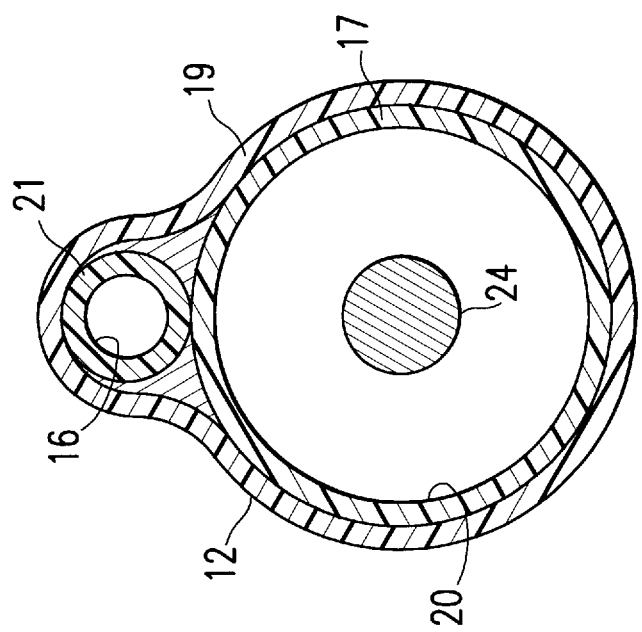
FIG. 2 is a transverse cross-sectional view of the catheter shown in FIG. 1 taken along the lines 2—2.

Reference is made to FIGS. 1–3 which illustrate a dilatation catheter 10 embodying features of the invention. The catheter 10 has an elongated shaft 11 with proximal and distal shaft sections 12 and 13, an adapter 14 on the proximal end of the shaft and a dilatation balloon 15 on the distal shaft section spaced proximal to the distal end. An inflation lumen 16 extends between the proximal end of the shaft 11 and a location spaced proximal to the distal end where it is in fluid communication with the interior of the dilatation balloon 15. The catheter shaft 11 is provided with a first inner tubular member 17 which has an expanded helical support coil 18 extending at least within its distal portion and an outer jacket or coating 19 of suitable polymeric material disposed about the coil. A guidewire receiving lumen 20 extends within both the proximal and distal shaft sections 12 and 13 and in the distal shaft section is defined at least in part by the first inner tubular member. The distal shaft section 13 is provided with a second inner tubular member 21 which defines the inflation lumen 16 therein.

Elongated sections of the outer jacket 19 and any materials between adjacent turns of the helical support coil 18 are readily removed by suitable means such as a CO, $CO_2$ Eximer lasers with an emitting light having a wave length of about 0.1 to about 12 microns. If desired, other types of lasers with emitting light with shorter wavelengths or other means may be employed to remove portions of the metallic coil 18 which are exposed. The application of laser energy is preferred because it readily removes the polymeric materials without affecting the helical coil, leaving clean perfusion ports 22 between the adjacent turns of the helical coil 18 which are in fluid communication with the guidewire receiving lumen 20. The portion of the outer jacket 19 which is removed to expose turns the helical coil 18 may vary in length from about 2 to about 30 cm, preferably about 5 to about 10 cm and in width from about 0.005 to about 0.02 inch (0.13–0.51 mm), preferably about 0.010 to about 0.015 inch (0.25–38 mm). A pair of elongated lengths of the outer jacket 19 may be removed or a plurality of pairs of shorter lengths of the outer jacket may be removed to expose desired portions of the helical support coil 18.

The outer jacket 19 may be formed of suitable polymeric material such as polyethylene, a polyester such as Hytrel® (trademark of Dupont), polyetheretherketone (PEEK) or a variety of other polymeric materials. Usually there is a polymer lining 23 (shown in FIG. 3) within the expanded helical coil 18 to present a smooth and preferably lubricous surface to the guidewire 24 which is advanced through the lumen 20 extending therein. The polymer lining may be formed of the same material as the jacket 19 or a lubricous material such a fluoropolymer or a hydrophilic material such as the ethylene-ethyl acrylate copolymer described in copending application Ser. No. 08/279,239, filed on Jul. 22,1994 which is incorporated herein by reference. The helical support coil is preferably a helically shaped ribbon formed of stainless steel, superelastic or shape memory NiTi and other suitable high strength materials such as high strength polymers. The ribbon from which the coil is shaped generally has a rectangular transverse cross-section of about 0.001 by about 0.003 inch (0.025–0.076 mm). The distance between turns of the helical coil which define the proximal perfusion ports 22 generally is about 0.0125 inch (0.3 mm).

Figure 4:
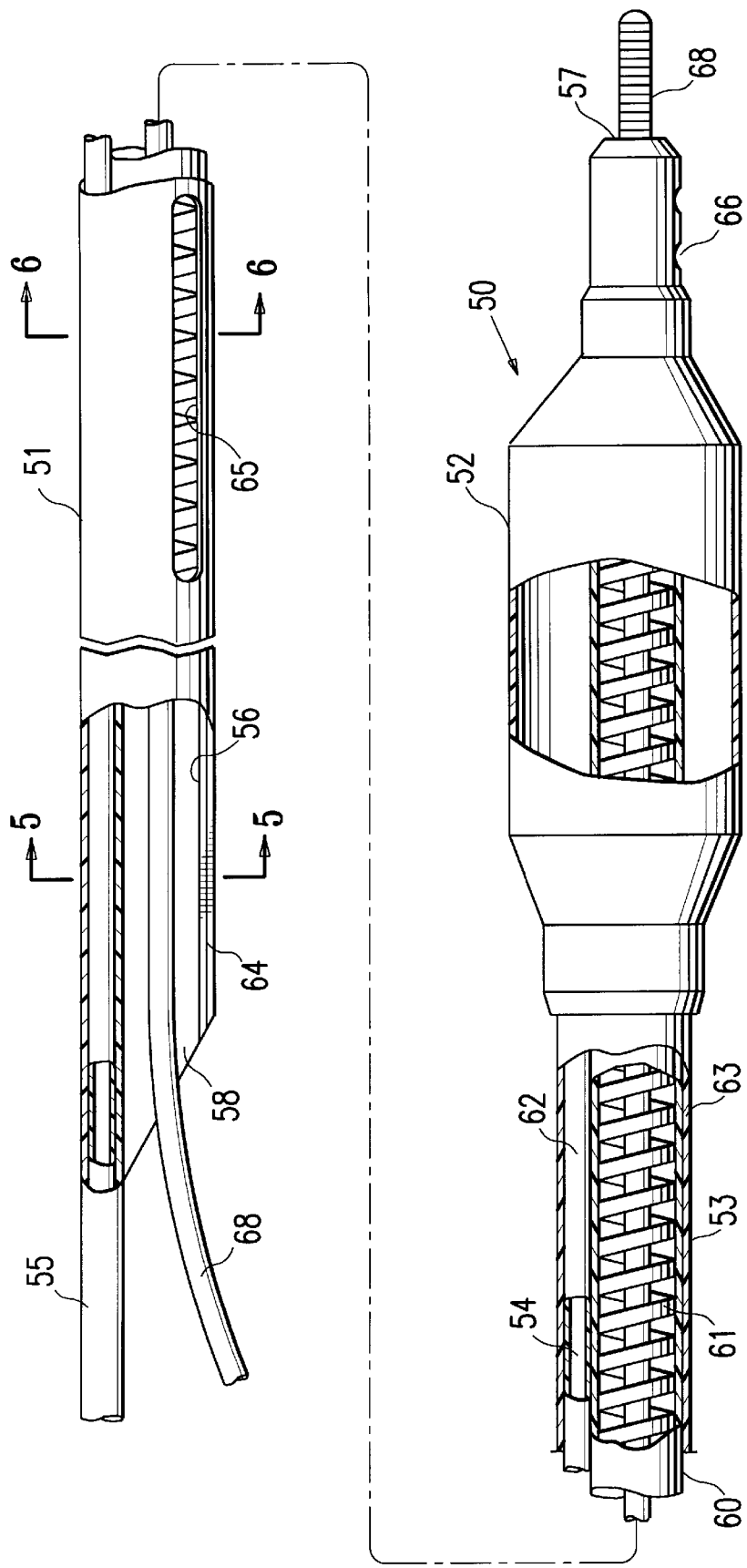
FIG. 4 is an elevational view, partially in section, of the distal portion of an alternate embodiment of the invention.
Figure 6:
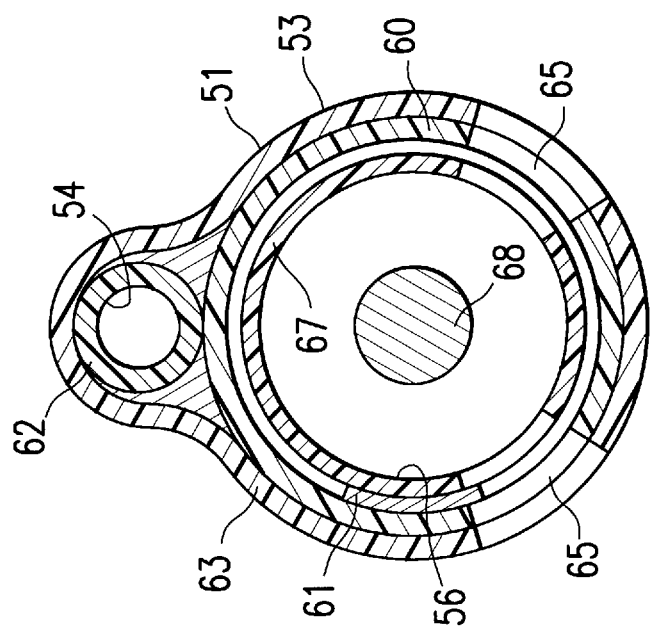
FIG. 6 is a transverse cross-sectional view of the embodiment shown in FIG. 4 taken along the lines 6—6.
Figure 5:
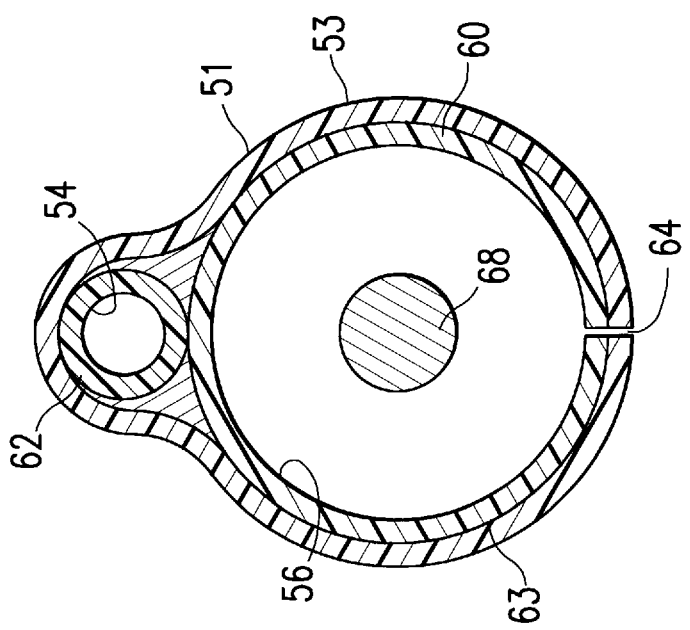
FIG. 5 is a transverse cross-sectional view of the embodiment shown in FIG. 4 taken along the lines 5—5.

FIGS. 4–6 illustrate another embodiment of the invention wherein the perfusion dilatation catheter 50 is provided with rapid exchange characteristics such as described in U.S. Pat. No. 5,496,275 (Sirhan et al.) and U.S. application Ser. No. 08/183,574, filed on Jan. 18, 1994 which have been incorporated herein. The catheter 50 generally has an elongated catheter shaft 51 and an inflatable dilatation balloon 52 on the distal shaft section 53. An inflation lumen 54 extends within the proximal-shaft section 55 and the distal shaft section 53 to a location spaced proximal to the distal end of the catheter shaft 51 and is in fluid communication with the interior of the balloon 52. A guidewire receiving lumen 56 extends within the distal shaft section 53 from the distal port 57 in the distal end of the catheter shaft 51 to a proximal port 58 spaced proximal to the distal end.

The distal shaft section 53 has a first tubular member 60 which surrounds supporting helical coil 61, a second tubular member 62 which defines the inflation lumen 54 and an outer jacket 63 which surrounds and secures together the first and second tubular members. A slit 64 is preferably provided through the walls of the first tubular member 60 and the outer jacket 63 from the proximal port 58 to a location spaced proximal to the portion of the distal shaft section having the helical support coil 61. When a slit 64 is provided the adjacent edges of the first tubular member 60 and the outer jacket 63 should be bonded together by suitable means such as an adhesive or a fusion bond to prevent delamination or separation in use. See for example the discussions found in U.S. Pat. No. 5,496,275 which is incorporated herein in its entirety by reference. The outer jacket 63 is preferably bonded to a substantial portion of the first inner tubular member 60 in which it is in contact as described in the above mentioned U.S. Pat. No. 5,496,275.

Proximal perfusion ports 65 are provided between adjacent turns of the helical support coil 61 as in the first embodiment by removing the outer jacket 63 along one or more lengths of the distal shaft section as in the previously discussed embodiment. Distal perfusion ports 66 are provided in the distal shaft section 53 distal to the balloon 52. As shown in FIG. 6, a third inner tubular member 67, preferably formed of lubricous material or having a lubricous inner surface, is preferably disposed within the helical support coil 61 to facilitate slidably reception of a guidewire 68.

To the extent not described herein or in U.S. Pat. No. 5,496,275, which has been incorporated herein, the dimensions, structural details and materials of construction may follow conventional practice for intravascular devices, such as catheters used in angioplasty procedures.

Various changes and modification may be made to the present invention without departing from the scope of the invention. Moreover, although individual features of the several embodiments of the invention may be shown in some of the drawings and not in others, those skilled in the art will recognize that individual features of one embodiment of the invention can be combined with any or all the features of another embodiment.

What is claimed is:

1. A balloon dilatation catheter having perfusion capabilities, comprising:

a) an elongated shaft having proximal and distal ends, proximal and distal shaft sections, a port in the distal end, a first inner lumen extending within at least the distal shaft section to the port in the distal end which is configured to slidably receive a guidewire therein and a second inner lumen extending through the proximal shaft section and the distal shaft section to a location in the distal shaft section spaced from the distal end;

b) an inflatable balloon on the distal shaft section having an interior in fluid communication with the second inner lumen;

c) an expanded helical coil supporting the first inner lumen within the distal shaft section, and d) a plurality of elongated perfusion ports in the distal catheter shaft section proximal to the inflatable balloon, at least one of said elongated perfusion ports exposing a plurality of turns of the expanded helical coil and being in fluid communication with the first inner lumen extending within the distal shaft section.

2. The balloon dilatation catheter of claim 1 including at least one pair of said elongated perfusion ports being on opposite sides of the distal shaft section.

3. The balloon dilatation catheter of claim 1 wherein at least one of said elongated perfusion ports is about 2 to about 30 cm in length.

4. The balloon dilatation catheter of claim 1 wherein at least one of said elongated perfusion ports is about 5 to about 10 cm in length.

5. The balloon dilatation catheter of claim 1 wherein at least one of said elongated perfusion ports is about 0.005 to about 0.02 inch in width.

6. The balloon dilatation catheter of claim 1 wherein at least one of said elongated perfusion ports is about 0.01 to about 0.015 inch in width.

* * * * *